(12) United States Patent
Arambula et al.

(10) Patent No.: US 7,785,253 B1
(45) Date of Patent: Aug. 31, 2010

(54) SURGICAL ACCESS SYSTEM AND RELATED METHODS

(75) Inventors: Jared Arambula, San Diego, CA (US); Eric Finley, Lancaster, CA (US); Scot Martinelli, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 37 days.

(21) Appl. No.: 11/344,711

(22) Filed: Jan. 31, 2006

Related U.S. Application Data

(60) Provisional application No. 60/648,849, filed on Jan. 31, 2005.

(51) Int. Cl.
*A61B 1/32* (2006.01)

(52) U.S. Cl. ...................................... 600/219

(58) Field of Classification Search .................. 600/212, 600/213, 214, 219, 222, 223, 224, 227, 231–237, 600/201
See application file for complete search history.

(56) References Cited

U.S. PATENT DOCUMENTS

| | | | |
|---|---|---|---|
| 1,548,184 A | 8/1925 | Cameron | |
| 2,704,064 A | 3/1955 | Fizzell et al. | |
| 2,736,002 A | 2/1956 | Oriel | |
| 2,808,826 A | 10/1957 | Reiner et al. | |
| 3,364,929 A | 1/1968 | Ide et al. | |
| 3,664,329 A | 5/1972 | Naylor | |
| 3,682,162 A | 8/1972 | Colyer | |
| 3,785,368 A | 1/1974 | McCarthy et al. | |
| 3,830,226 A | 8/1974 | Staub et al. | |
| 3,957,036 A | 5/1976 | Normann | |
| 4,099,519 A | 7/1978 | Warren | |
| 4,164,214 A | 8/1979 | Stark et al. | |
| 4,207,897 A | 6/1980 | Lloyd et al. | |
| 4,224,949 A | 9/1980 | Scott et al. | |
| 4,235,242 A | 11/1980 | Howson et al. | |
| 4,285,347 A | 8/1981 | Hess | |
| 4,291,705 A | 9/1981 | Severinghaus et al. | |
| 4,461,300 A | 7/1984 | Christensen | |
| 4,515,168 A | 5/1985 | Chester et al. | |
| 4,519,403 A | 5/1985 | Dickhudt | |
| 4,545,374 A | 10/1985 | Jacobson | |
| 4,561,445 A | 12/1985 | Berke et al. | |

(Continued)

FOREIGN PATENT DOCUMENTS

EP 0972538 A2 1/2000

(Continued)

OTHER PUBLICATIONS

"Brackmann II EMG System", *Medical Electronics*, (1999),4 pages.

(Continued)

*Primary Examiner*—Cris L Rodriguez
*Assistant Examiner*—Hao D Mai
(74) *Attorney, Agent, or Firm*—Jonathan Spangler; Jay B. Bell

(57) ABSTRACT

A retractor-based access system for performing minimally invasive spine surgery via an anterior approach. The anterior access system and related methods of the present invention involve a plurality of retractor blades under the control of a single retractor handle apparatus.

24 Claims, 10 Drawing Sheets

U.S. PATENT DOCUMENTS

| | | | |
|---|---|---|---|
| 4,562,832 A | 1/1986 | Wilder et al. | |
| 4,573,448 A | 3/1986 | Kambin | |
| 4,592,369 A | 6/1986 | Davis et al. | |
| 4,595,018 A | 6/1986 | Rantala | |
| 4,633,889 A | 1/1987 | Talalla et al. | |
| 4,658,835 A | 4/1987 | Pohndorf | |
| 4,744,371 A | 5/1988 | Harris | |
| 4,759,377 A | 7/1988 | Dykstra | |
| 4,807,642 A | 2/1989 | Brown | |
| 4,892,105 A | 1/1990 | Prass | |
| 4,926,865 A | 5/1990 | Oman | |
| 4,949,707 A * | 8/1990 | LeVahn et al. | 600/234 |
| 4,962,766 A | 10/1990 | Herzon | |
| 4,964,411 A | 10/1990 | Johnson et al. | |
| 5,007,902 A | 4/1991 | Witt | |
| 5,058,602 A | 10/1991 | Brody | |
| 5,081,990 A | 1/1992 | Deletis | |
| 5,092,344 A | 3/1992 | Lee | |
| 5,127,403 A | 7/1992 | Brownlee | |
| 5,161,533 A | 11/1992 | Prass et al. | |
| 5,196,015 A | 3/1993 | Neubardt | |
| RE34,390 E | 9/1993 | Culver | |
| 5,255,691 A | 10/1993 | Otten | |
| 5,282,468 A | 2/1994 | Klepinski | |
| 5,284,153 A | 2/1994 | Raymond et al. | |
| 5,284,154 A | 2/1994 | Raymond et al. | |
| 5,299,563 A | 4/1994 | Seton | |
| 5,312,417 A | 5/1994 | Wilk | |
| 5,313,956 A | 5/1994 | Knutsson et al. | |
| 5,327,902 A | 7/1994 | Lemmen | |
| 5,333,618 A | 8/1994 | Lekhtman et al. | |
| 5,375,067 A | 12/1994 | Berchin | |
| 5,383,876 A | 1/1995 | Nardella | |
| 5,474,558 A | 12/1995 | Neubardt | |
| 5,480,440 A | 1/1996 | Kambin | |
| 5,482,038 A | 1/1996 | Ruff | |
| 5,484,437 A | 1/1996 | Michelson | |
| 5,540,235 A | 7/1996 | Wilson | |
| 5,549,656 A | 8/1996 | Reiss | |
| 5,560,372 A | 10/1996 | Cory | |
| 5,566,678 A | 10/1996 | Cadwell | |
| 5,579,781 A | 12/1996 | Cooke | |
| 5,593,429 A | 1/1997 | Ruff | |
| 5,599,279 A | 2/1997 | Slotman et al. | |
| 5,630,813 A | 5/1997 | Kieturakis | |
| 5,671,752 A | 9/1997 | Sinderby et al. | |
| 5,707,359 A | 1/1998 | Bufalini | |
| 5,711,307 A | 1/1998 | Smits | |
| 5,728,046 A | 3/1998 | Mayer et al. | |
| 5,741,253 A | 4/1998 | Michelson | |
| 5,759,159 A | 6/1998 | Masreliez | |
| 5,772,661 A | 6/1998 | Michelson | |
| 5,775,331 A | 7/1998 | Raymond et al. | |
| 5,779,642 A | 7/1998 | Nightengale | |
| 5,785,658 A | 7/1998 | Benaron et al. | |
| 5,797,854 A | 8/1998 | Hedgecock | |
| 5,814,073 A | 9/1998 | Bonutti | |
| 5,830,151 A | 11/1998 | Hadzic et al. | |
| 5,851,191 A | 12/1998 | Gozani | |
| 5,853,373 A | 12/1998 | Griffith et al. | |
| 5,860,973 A | 1/1999 | Michelson | |
| 5,862,314 A | 1/1999 | Jeddeloh | |
| 5,872,314 A | 2/1999 | Clinton | |
| 5,885,219 A | 3/1999 | Nightengale | |
| 5,888,196 A | 3/1999 | Bonutti | |
| 5,902,231 A | 5/1999 | Foley et al. | |
| 5,928,139 A | 7/1999 | Koros et al. | |
| 5,928,158 A | 7/1999 | Aristides | |
| 5,976,094 A | 11/1999 | Gozani | |
| 6,004,262 A | 12/1999 | Putz et al. | |
| 6,024,697 A * | 2/2000 | Pisarik | 600/224 |
| 6,027,456 A | 2/2000 | Feler et al. | |
| 6,038,477 A | 3/2000 | Kayyali | |
| 6,050,992 A | 4/2000 | Nichols | |
| 6,074,343 A | 6/2000 | Nathanson et al. | |
| 6,083,154 A * | 7/2000 | Liu et al. | 600/234 |
| 6,104,957 A | 8/2000 | Alo et al. | |
| 6,120,503 A | 9/2000 | Michelson | |
| 6,132,386 A | 10/2000 | Gozani et al. | |
| 6,132,387 A | 10/2000 | Gozani et al. | |
| 6,135,965 A | 10/2000 | Tumer et al. | |
| 6,146,335 A | 11/2000 | Gozani | |
| 6,161,047 A | 12/2000 | King et al. | |
| 6,206,826 B1 | 3/2001 | Mathews et al. | |
| 6,224,549 B1 | 5/2001 | Drongelen | |
| 6,259,945 B1 | 7/2001 | Epstein et al. | |
| 6,266,558 B1 | 7/2001 | Gozani et al. | |
| 6,292,701 B1 | 9/2001 | Prass et al. | |
| 6,306,100 B1 | 10/2001 | Prass | |
| 6,312,392 B1 | 11/2001 | Herzon | |
| 6,325,764 B1 | 12/2001 | Griffith et al. | |
| 6,334,068 B1 | 12/2001 | Hacker | |
| 6,425,901 B1 | 7/2002 | Zhu et al. | |
| 6,466,817 B1 | 10/2002 | Kaula et al. | |
| 6,500,128 B2 | 12/2002 | Marino | |
| 6,564,078 B1 | 5/2003 | Marino et al. | |
| 6,760,616 B2 | 7/2004 | Hoey et al. | |
| 6,869,398 B2 * | 3/2005 | Obenchain et al. | 600/224 |
| 6,902,569 B2 | 6/2005 | Parmer et al. | |
| 6,929,606 B2 | 8/2005 | Ritland | |
| 7,050,848 B2 | 5/2006 | Hoey et al. | |
| 7,079,883 B2 | 7/2006 | Marino et al. | |
| 2002/0007129 A1 | 1/2002 | Marino | |
| 2002/0072686 A1 | 6/2002 | Hoey et al. | |
| 2002/0161415 A1 | 10/2002 | Cohen et al. | |
| 2002/0177753 A1 * | 11/2002 | Dobrovolny | 600/234 |
| 2005/0004593 A1 | 1/2005 | Simonson | |
| 2005/0004623 A1 | 1/2005 | Miles et al. | |
| 2005/0075578 A1 | 4/2005 | Gharib et al. | |
| 2005/0149035 A1 | 7/2005 | Pimentra et al. | |
| 2005/0182454 A1 | 8/2005 | Gharib et al. | |
| 2006/0025703 A1 | 2/2006 | Miles et al. | |
| 2006/0069315 A1 | 3/2006 | Miles et al. | |
| 2006/0224078 A1 | 10/2006 | Hoey et al. | |

FOREIGN PATENT DOCUMENTS

| | | |
|---|---|---|
| WO | WO-0038574 A1 | 7/2000 |
| WO | WO-0066217 A1 | 11/2000 |
| WO | WO-0137728 A1 | 5/2001 |
| WO | WO-03037170 A3 | 5/2003 |
| WO | WO-2005013805 A3 | 2/2005 |
| WO | WO-2006042241 A2 | 4/2006 |

OTHER PUBLICATIONS

"Electromyography System", *International Search Report*, International Application No. PCT/US00/32329,(Apr. 27, 2001),9 pages.

"Nerve Proximity and Status Detection System and Method", *International Search Report*, International Application No. PCT/US01/18606,(Oct. 18, 2001),6 pages.

"Neurovision SE Nerve Locator/Monitor", *RLN Systems, Inc. Operators Manual*, (1999),22 pages.

"Relative Nerve Movement and Status Detection System and Method", *International Search Report*, International Application No. PCT/US01/18579,(Jan. 15, 2002),6 pages.

"System and Method for Determining Nerve Proximity, Direction, and Pathology During Surgery", *International Search Report*, International Application No. PCT/US02/22247,(Mar. 27, 2003),4 pages.

"System and Methods for Determining Nerve Direction to a Surgical Instrument", *International Search Report*, International Application No. PCT/US03/02056,(Aug. 12, 2003),5 pages.

"Systems and Methods for Performing Percutaneous Pedicle Integrity Assessments", *International Search Report*, International Application No. PCT/US02/35047,(Aug. 11, 2003),5 pages.

"Systems and Methods for Performing Surgery Procedures and Assessments", International Search Report, International Application No. PCT/US02/30617,(Jun. 5, 2003),4 pages.

"The Brackmann II EMG Monitoring System", *Medical Electronics Co. Operator's Manual Version 1.1*, (1996),50 pages.

"The Nicolet Vliking IV", *Nicolet Biomedical Products*, (1999),6 pages.

Anderson, D. G., et al., "Pedicle screws with high electrical resistance: a potential source of error with stimulus-evoked EMG", *Spine*, 27(14):, Department of Orthopaedic Surgery, University of Virginia,(Jul. 15, 2002),1577-1581.

Bose, Bikash, et al., "Neurophysiologic Monitoring of Spinal Nerve Root Function During Instrumented Posterior Lumbar Spine Surgery", *Spine*, 27(13),(2002),1444-1450.

Calancie, Blair, et al., "Stimulus-Evoked EMG Monitoring During Transpedicular Lumbosacral Spine Instrumentation", *Spine*, 19(24), (1994),2780-2786.

Clements, David, et al., "Evoked and Spontaneous Electromyography to Evaluate Lumbosacral Pedicle Screw Placement", *Spine*, 21(5), (1996),600-604.

Danesh-Clough, T., "The use of evoked EMG in detecting misplaced thoracolumbar pedicle screws" *Spine*, 26(12), Orthopaedic Department, Dunedin Hospital,(Jun. 15, 2001),1313-1316.

Darden, B.V., et al., "A comparison of impedance and electromyogram measurements in detecting the presence of pedide wall breakthrough", *Spine*, 23(2), Charlotte Spine Center, North Carolina,(Jan. 15, 1998),256-262.

Ebraheim, N. A., et al., "Anatomic relations between the lumbar pedicle and the adjacent neural structures", *Spine*, 22(20), Department of Orthopaedic Surgery, Medical College of Ohio,(Oct. 15, 1997),2338-2341.

Ford, Douglas, "Electrical Characteristics of Peripheral Nerve Stimulators Implications for Nerve Localization", *Regional Anesthesia*, 9, (1984),73-77.

Glassman, Steven, "A Prospective Analysis of Intraoperative Electromyographic Monitoring of Pedicle Screw Placement With Computed Tomographic Scan Confirmation", *Spine*, 20(12),(1995),1375-1379.

Greenblatt, Gordon, "Needle Nerve Stimulator-Locator: Nerve Blocks with a New Instrument for Locating Nerves", *Anesthesia & Analgesia*, 41(5),(1962),599-602.

Haig, "Point of view", *Spine 27* (24),2819.

Haig, A. J., et al., "The relation among spinal geometry on MRI, paraspinal electromyographic abnormalities, and age in persons referred for electrodiagnostic testing of low back symptoms", *Spine*, 27(17), Department of Physical Medicine and Rehabilitation, University of Michigan,(Sep. 1, 2002).1918-1925.

Holland, N. R., et al., "Higher electrical stimulus Intensities are required to activate chronically compressed nerve roots. Implications for intraoperative electromyographic pedicle screw testing", *Spine*, 23(2), Department of Neurology, Johns Hopkins University School of Medlcine,(Jan 15, 1998),224-227.

Holland, Neil, "Intraoperative Electromyography During Thoracolumbar Spinal Surgery", *Spine*, 23(17) (1998),1915-1922.

Journee, H. L., et al., "System for Intra-Operative Monitoring of the Cortical Integrity of the Pedicle During Screw Placement in Low-Back Surgery: Design and Clinical Results", *Sensory and neuromuscular diagnostic instrumentation end data analysis. 18th Annual International Conference on Engineering in Medicine and Biology Society*, 1(31), (Oct. 1996),144-145.

Lenke, Lawrence, "Triggered Electromyographic Threshold for Accuracy of Pedicle Screw Placement", *Spine*, 20 (14), (1995),1585-1591.

Maguire, J., et al., "Evaluation of Intrapedicular Screw Position Using Intraoperative Evoked Electromyography", *Spine*, 20(9), (1995),1068-1074.

Martin, David, et al., "Initiation of Erection and Semen Release by Rectal Probe Electrostimulation (RPE) ", *The Williams & Wilkins Co.*,(1983),637-642.

Minahan, R. E., et al., "The effect of neuromuscular blockade on pedicle screw stimulation thresholds", *Spine*, 25(19), Johns Hopkins University, School of Medicine,(Oct. 1, 2000),2526-2530.

Pither, Charles, et al., "The Use of Peripheral Nerve Stimulators for Regional Anesthesia: Review of Experimental Characteristics, Technique, and Clinical Applications", *Regional Anesthesia*, (1985),10:47-53.

Raj, P., et al., "Infraclavicular Brachial Plexus Block—A New Approach", *Anesthesia and Analgesia*, (52)6, (1973),897-904.

Raj, P., et al., "The Use of Peripheral Nerve Stimulators for Regional Anesthesia", *Clinical Issues In Regional Anesthesia*, 1 (4), (1985),1-6.

Raj, P., et al., "Use of The nerve Stimulator of Peripheral Blocks", *Regional Anesthesia*, (Apr.-Jun. 1980),14-21.

Raymond, Stephen, et al., "The Nerve Seeker: A System for Automated Nerve Localization", *Regional Anesthesia*, 17(3), (1992),151-162.

Shafik, Ahmed, "Cavernous Nerve Simulation through an Extrapelvic Subpubic Approach: Role in Pencil Erection", *Eur. Urol*, 26,(1994),98-102.

Toleikis, J., et al., "The Usefulness of Electrical Stimulation for Assessing Pedicle Screw Replacements", *Journal of Spinal Disorder*, 13(4), (2000),283-289.

* cited by examiner

SURGICAL ACCESS SYSTEM AND RELATED METHODS

CROSS REFERENCES TO RELATED APPLICATIONS

The present nonprovisional patent application claims benefit of priority under 35 U.S.C. §119(e) from commonly owned and co-pending U.S. Provisional Application Ser. No. 60/648,849, entitled "Surgical Access System and Related Methods," filed on Jan. 31, 2005, the entire contents of which are hereby expressly incorporated by reference into this disclosure as if set forth fully herein. The present application also incorporates by reference the following co-pending and co-assigned patent applications in their entireties: PCT App. Ser. No. PCT/US02/22247, entitled "System and Methods for Determining Nerve Proximity, Direction, and Pathology During Surgery," filed on Jul. 11, 2002; PCT App. Ser. No. PCT/US02/30617, entitled "System and Methods for Performing Surgical Procedures and Assessments," filed on Sep. 25, 2002; PCT App. Ser. No. PCT/US02/35047, entitled "System and Methods for Performing Percutaneous Pedicle Integrity Assessments," filed on Oct. 30, 2002; and PCT App. Ser. No. PCT/US03/02056, entitled "System and Methods for Determining Nerve Direction to a Surgical Instrument," filed Jan. 15, 2003 (collectively "NeuroVision PCT Applications"); PCT App. Ser. No. PCT/US2004/031768, entitled "Surgical Access System and Related Methods," filed on Sep. 27, 2004; and PCT App. Ser. No. PCT/US2005/036454, entitled "Surgical Access System and Related Methods," filed Oct. 11, 2005 (collectively "Maxcess PCT Applications").

BACKGROUND OF THE INVENTION

I. Field of the Invention

The present invention relates to accessing a surgical target site in order to perform surgical procedures.

II. Discussion of the Prior Art

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity and cost associated with such procedures. The access systems developed to date, however, fail in various respects to meet all the needs of the surgeon population. The present invention is directed at this need.

SUMMARY OF THE INVENTION

The present invention accomplishes this goal by providing a retractor-based access system for performing minimally invasive spine surgery via an anterior approach. The anterior access system and related methods of the present invention involve a plurality of retractor blades under the control of a single retractor handle apparatus.

According to one broad aspect of the present invention, the access system comprises a tissue retraction assembly capable of being introduced into a distracted region to thereby define and establish an operative corridor. Once established, any of a variety of surgical instruments, devices, or implants may be passed through and/or manipulated within the operative corridor depending upon the given surgical procedure. The tissue retraction assembly may include any number of components capable of performing the necessary retraction. By way of example only, the tissue retraction assembly may include one or more retractor blades extending from a handle assembly. The handle assembly may be manipulated to open the retractor assembly; that is, allowing the retractor blades to separate from one another (simultaneously or sequentially) to create an operative corridor to the surgical target site.

The retractor blades may optionally be equipped with a mechanism for transporting or emitting light at or near the surgical target site to aid the surgeon's ability to visualize the surgical target site, instruments and/or implants during the given surgical procedure. According to one embodiment, this mechanism may comprise, but need not be limited to, coupling one or more light sources to the retractor blades such that the terminal ends are capable of emitting light at or near the surgical target site. According to another embodiment, this mechanism may comprise, but need not be limited to, constructing the retractor blades of suitable material (such as clear polycarbonate) and configuration such that light may be transmitted generally distally through the walls of the retractor blade light to shine light at or near the surgical target site. This may be performed by providing the retractor blades having light-transmission characteristics (such as with clear polycarbonate construction) and transmitting the light almost entirely within the walls of the retractor blade (such as by frosting or otherwise rendering opaque portions of the exterior and/or interior) until it exits a portion along the interior (or medially-facing) surface of the retractor blade to shine at or near the surgical target site. The exit portion may be optimally configured such that the light is directed towards the approximate center of the surgical target site and may be provided along the entire inner periphery of the retractor blade or one or more portions therealong.

The retractor blades may also optionally be equipped with one or more electrodes for use in detecting the existence of (and optionally the distance and/or direction to) neural structures such that the operative corridor may be established through (or near) any of a variety of tissues having such neural structures which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed. These electrodes are preferably provided for use with a nerve surveillance system such as, by way of example, the "Neurovision PCT Applications" referenced below.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of spinal surgery, the surgical access system of the present invention may be employed in any number of anatomical settings to provide access to any number of different surgical target sites throughout the body. The surgical access system disclosed herein boasts a variety of inventive features and components that warrant patent protection, both individually and in combination.

Figure 1:
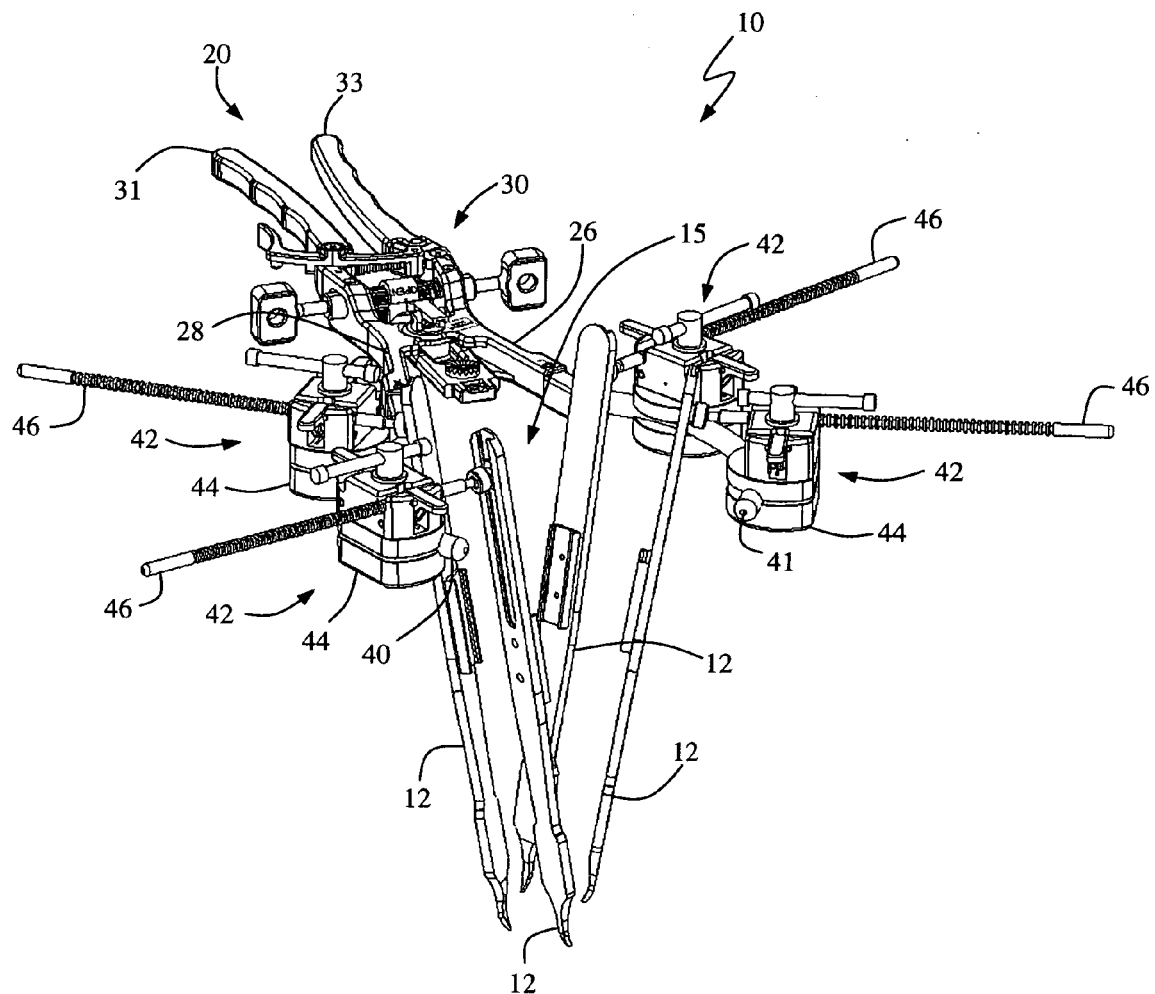
FIGS. 1-2 are perspective views of a tissue retraction assembly forming part of a surgical access system according to the present invention.
Figure 2:
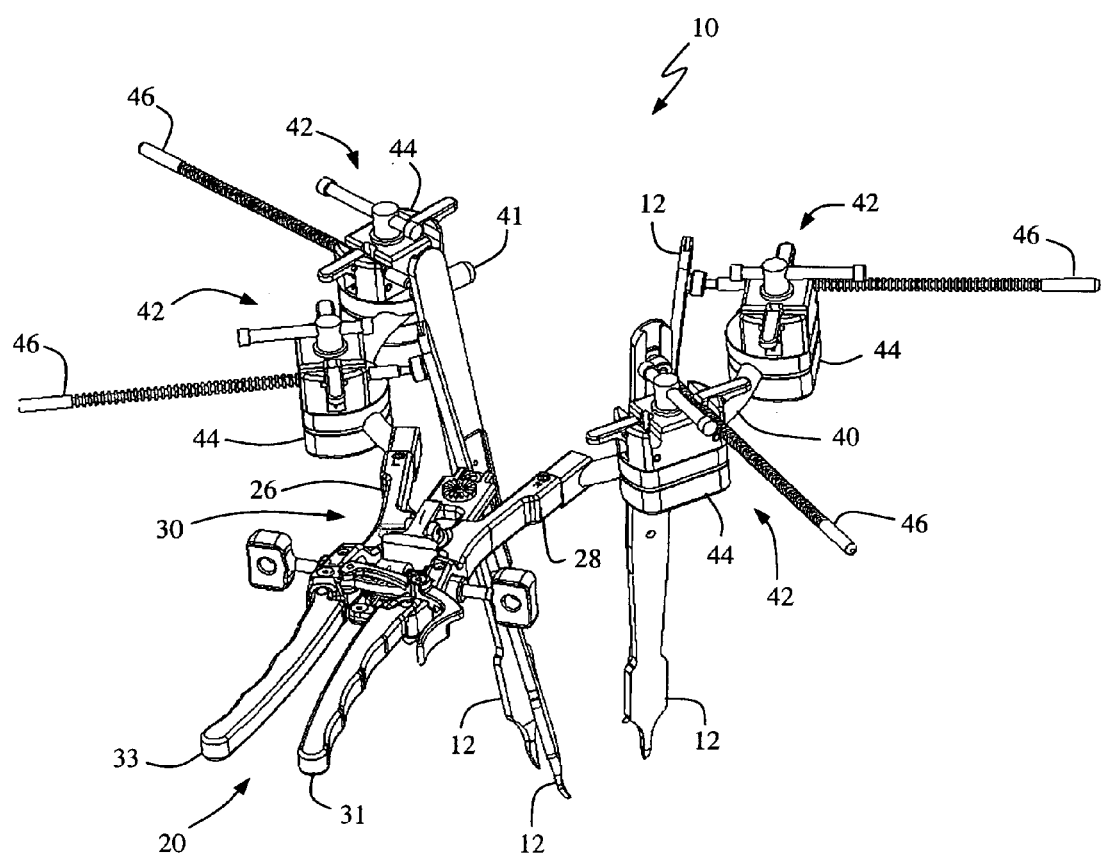
Figure 3:
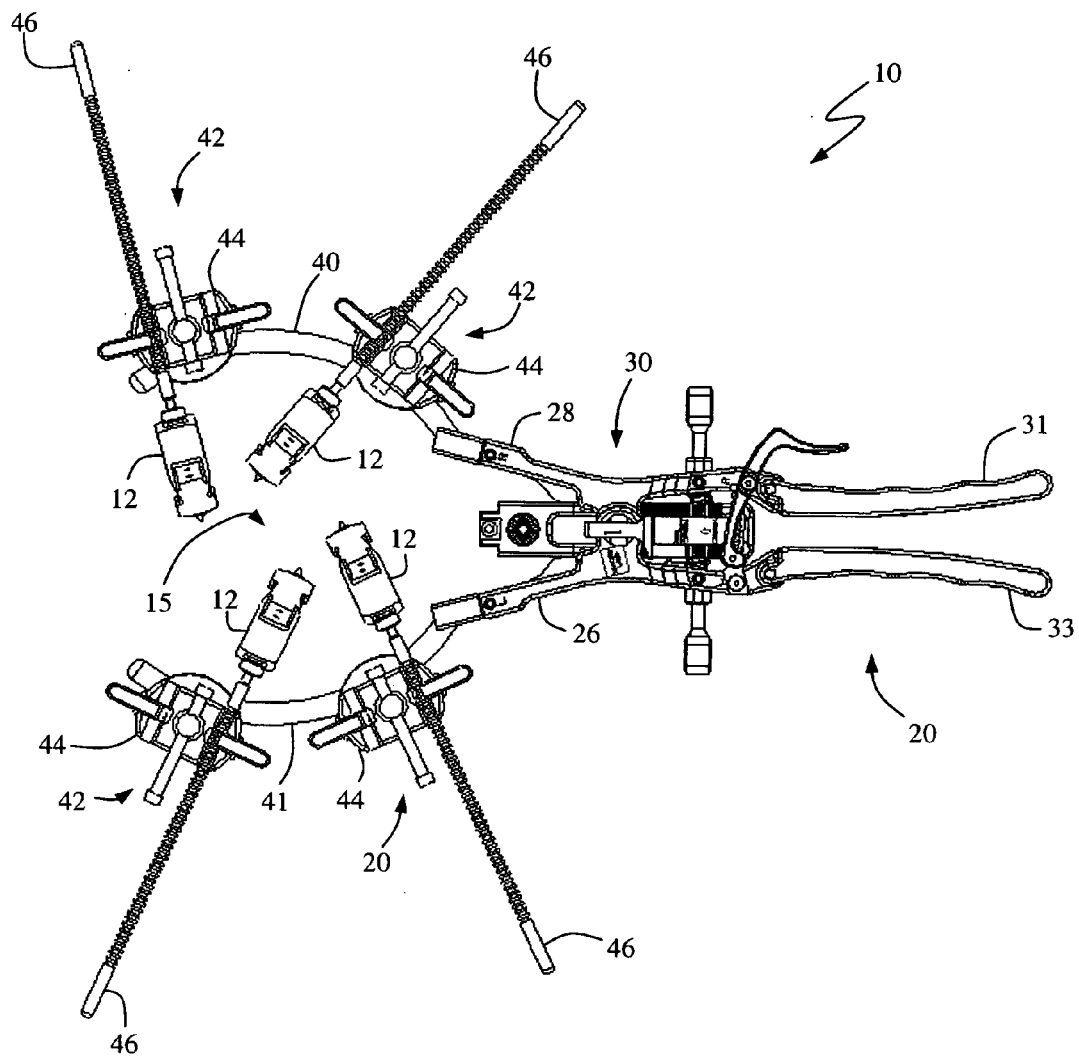
FIG. 3 is a top view of the tissue retraction assembly of FIGS. 1-2.

FIGS. 1-3 illustrate a tissue retraction assembly 10 forming part of a surgical access system according to one embodiment of the present invention. The tissue retraction assembly 10 includes a plurality of retractor blades 12 coupled to a handle assembly 20 via a plurality of blade holder assemblies 42. The tissue retraction assembly 10 is shown in a fully retracted or "open" configuration, with the retractor blades 12 positioned a distance from one another so as to form an operative corridor 15 therebetween and extending to a surgical target site (e.g. an annulus of an intervertebral disc). This is accomplished by initially creating a distraction corridor to a surgical target site via any anterior access method well known in the art, such as may be performed via a general or "access" surgeon. Once distracted, the resulting void or distracted region within the patient is of sufficient size to accommodate tissue retraction assembly 10 as described herein. More specifically, the distal ends of the retractor blades 12 are attached to (e.g. introduced into) target vertebrae on either side of an intervertebral space. With the retractor blades 12 so positioned, the proximal ends are attached to the blade holder assemblies 42 while the handle assembly 20 is in a first, "closed" position. At that point, the handle assembly 20 may be operated to move the retractor blades 12 into a second, "open" or "retracted" position to create the operative corridor 15 to the surgical target site (e.g. an intervertebral space). Although shown and described below with regard to a four-bladed configuration, it is to be readily appreciated that the number of retractor blades 12 may be increased or decreased without departing from the scope of the present invention. Moreover, although described and shown herein with reference to a generally anterior approach to a spinal surgical target site, it will be appreciated that the tissue retraction assembly 10 of the present invention may find use in any number of different surgical approaches, including generally posterior, generally postero-lateral, generally lateral and generally antero-lateral. According to a further aspect of the present invention, any or all of the retractor blades 12 may be provided with one or more electrodes 39 (preferably at their distal regions, shown more clearly in FIGS. 9-10) equipped for use with a nerve surveillance system, such as, by way of example, the type shown and described in the NeuroVision PCT Applications (referenced below).

Figure 4:
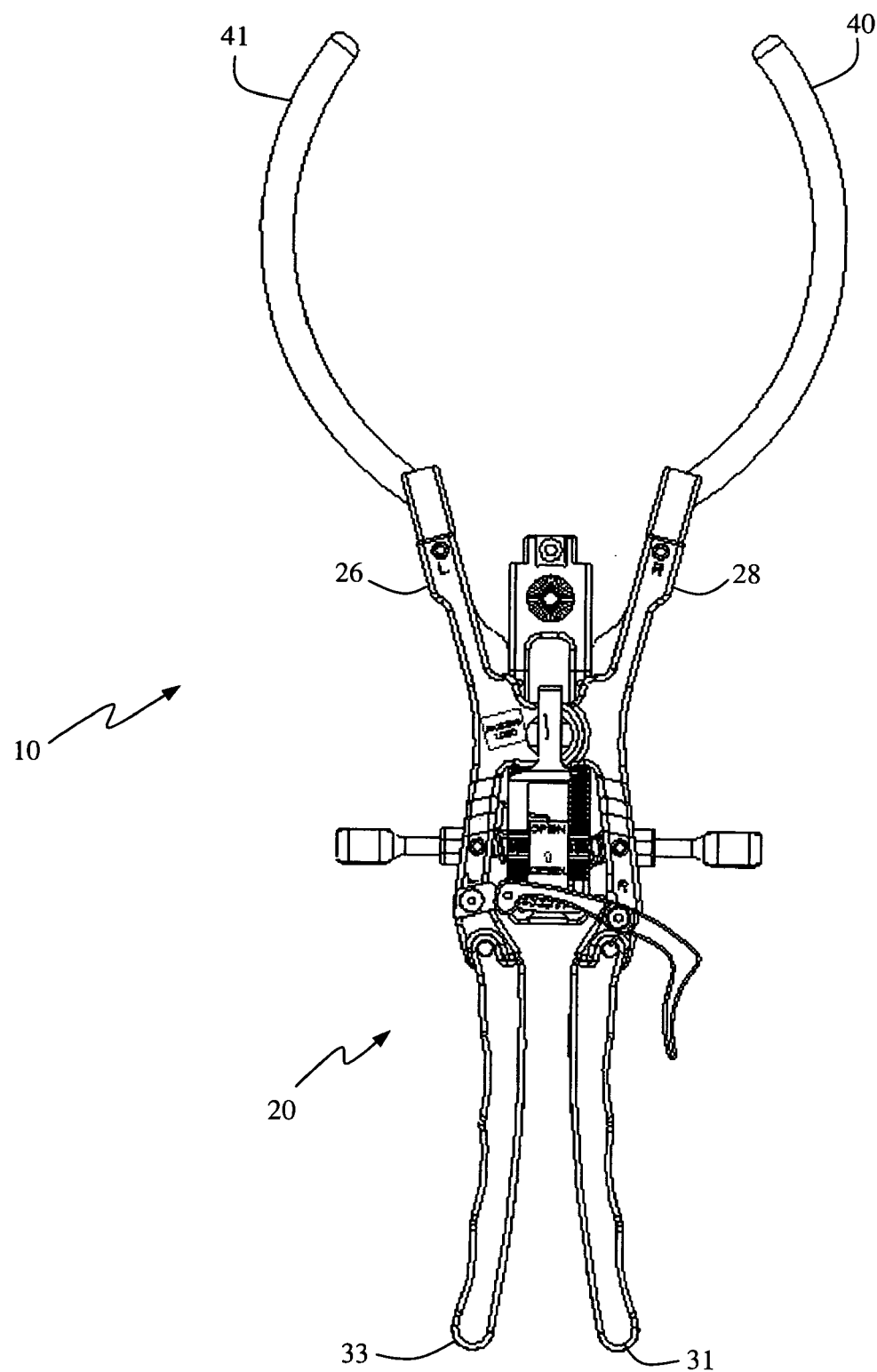
FIG. 4 is a top view of the tissue retraction assembly of FIG. 1 wherein the retractor blade assemblies have been removed.
Figure 5:
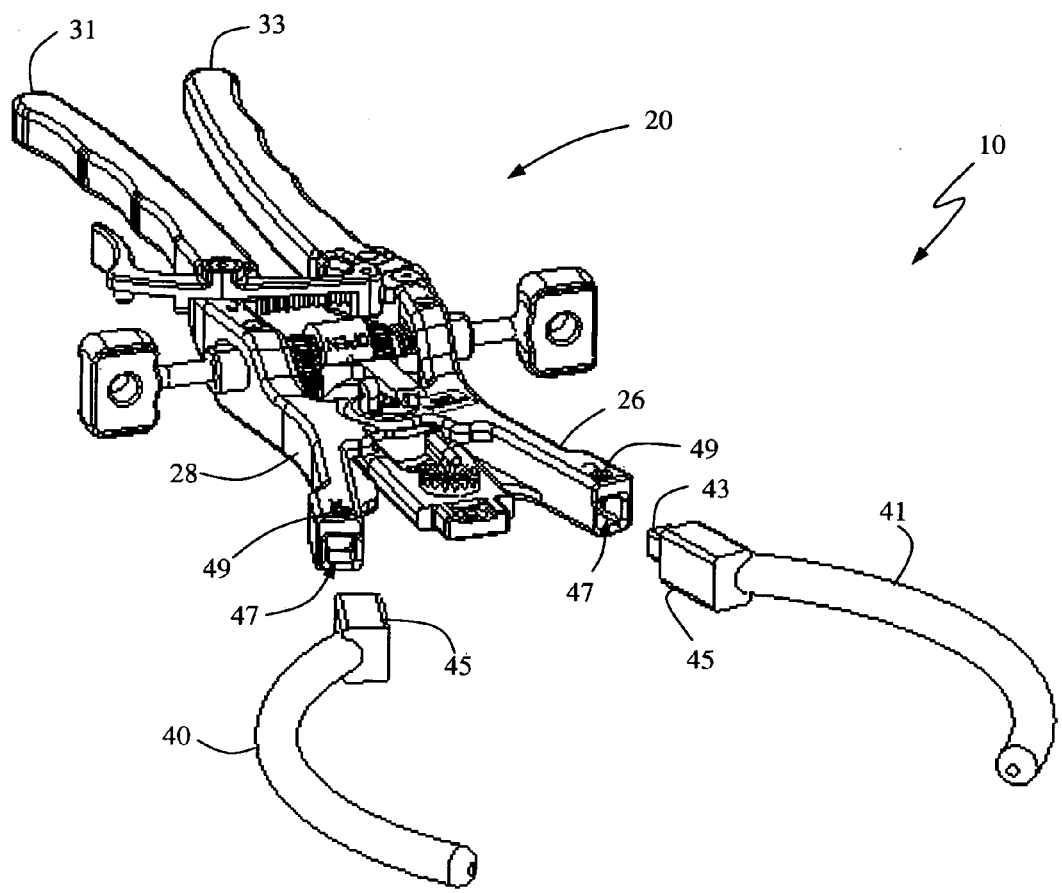
FIG. 5 is a perspective view of the tissue retraction assembly of FIG. 4, in which the half-ring assemblies are illustrated in an exploded view removed from the handle assembly.

In a preferred embodiment, the handle assembly 20 is substantially similar to the type shown and described in commonly owned and currently pending PCT App. Ser. No. PCT/US2004/031768, entitled "Surgical Access System and Related Methods," filed on Sep. 27, 2004, and U.S. Provisional Pat. App. Ser. No. 60/617,498, entitled "Surgical Access System and Related Methods," filed Oct. 8, 2004 (collectively "Maxcess Applications"), the entire contents of which are incorporated by reference into the present application as if disclosed herein. The handle assembly 20 may be coupled to any number of mechanisms for rigidly registering the handle assembly 20 in fixed relation to the operative site, such as by way of example only an articulating arm mounted to the operating table. The handle assembly 20 includes first and second arm members 26, 28 hingedly coupled via coupling mechanism shown generally at 30. The distal ends of first and second arm members 26, 28 may be equipped with arm extensions 40, 41 (shown more clearly in FIGS. 4-5). Arm extensions 40, 41 may be formed in any shape desired or required to ensure a suitable operating corridor, including but not limited to a generally curved or arcuate shape. Arm extensions 40, 41 may also be configured to couple to the first and second arm members 28, 26, respectively, via any number of suitable manners, including but not limited to providing coupling blocks 45 disposed on the proximal ends of the arm extensions 40, 41 with posts 43 extending therefrom for engagement into corresponding recesses 47 formed within the arm members 26, 28. This engagement between the posts 43 and recesses 47 may be augmented via the use of any number of suitable locking features, including but not limited to passing a set screw (not shown) through an aperture 49 in the arm 26, 28 such that the set screw (not shown) may be biased into the posts 43 after they have been introduced into the respective recess 47.

A plurality of blade holder assemblies 42 may be slideably attached to arm extensions 40. Blade holder assemblies 42 each include a base member 44 and a blade extender 46. Blade extenders 46 are generally elongated in shape and have a medial end dimensioned to slideably engage retractor blades 12. The retractor blades 12 are each coupled to a medial end of one of blade extenders 46. Thus, by extension, at least one retractor blade 12 is coupled to the end of the first arm member 26, and at least one retractor blade 12 is coupled to the end of the second arm member 28. Through the use of handle extenders 31, 33 (e.g., by forcing them towards one another) the arms 26, 28 may be simultaneously opened such that the blades 12 coupled to arm extensions 40, 41 move away from one another. In a still further aspect of the present invention, the arm extensions 40, 41 may be opened up before the retractor blades 12 are coupled thereto. That is, the blade extenders 46 may be manually moved in a generally lateral direction (that is, away from the plane of the distal tip of the blade 12) in order to create the operative corridor 15, at which point the blade extender 46 may be coupled to the blade holder assembly 42 to maintain this position. This may be done by moving the blades 12 sequentially or simultaneously (with at least two blades being moved at the same time). In any event, the dimension and/or shape of the operative corridor 15 may be tailored depending upon the degree to which the arms 26, 28 are opened. That is, the operative corridor 15 may be tailored to provide any number of suitable cross-sectional shapes, including but not limited to a generally circular cross-section, a generally ellipsoidal cross-section, and/or an oval cross-section.

Figure 6:
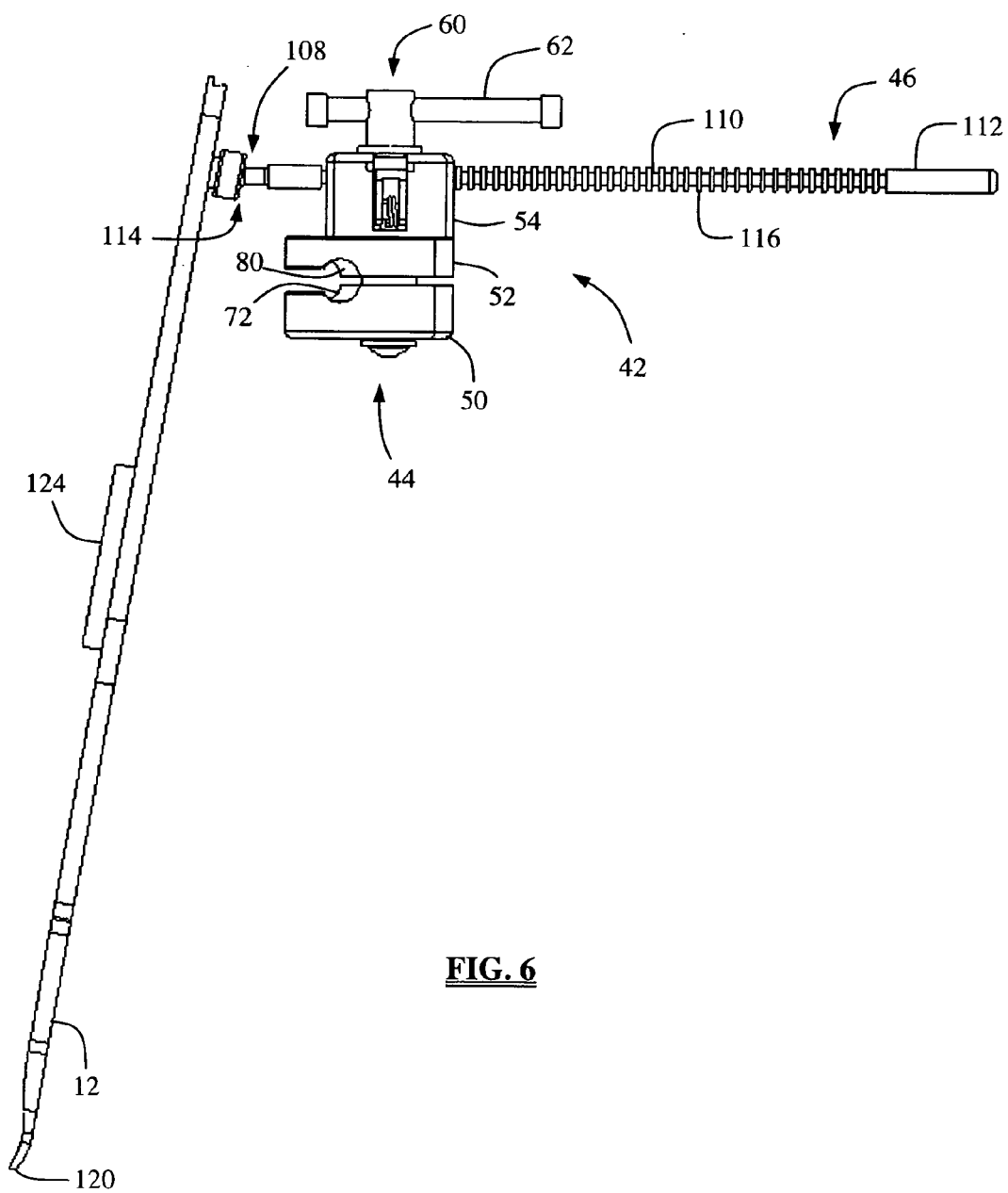
FIGS. 6-8 are side, perspective, and top views of a retractor blade assembly according to one embodiment of the present invention.
Figure 7:
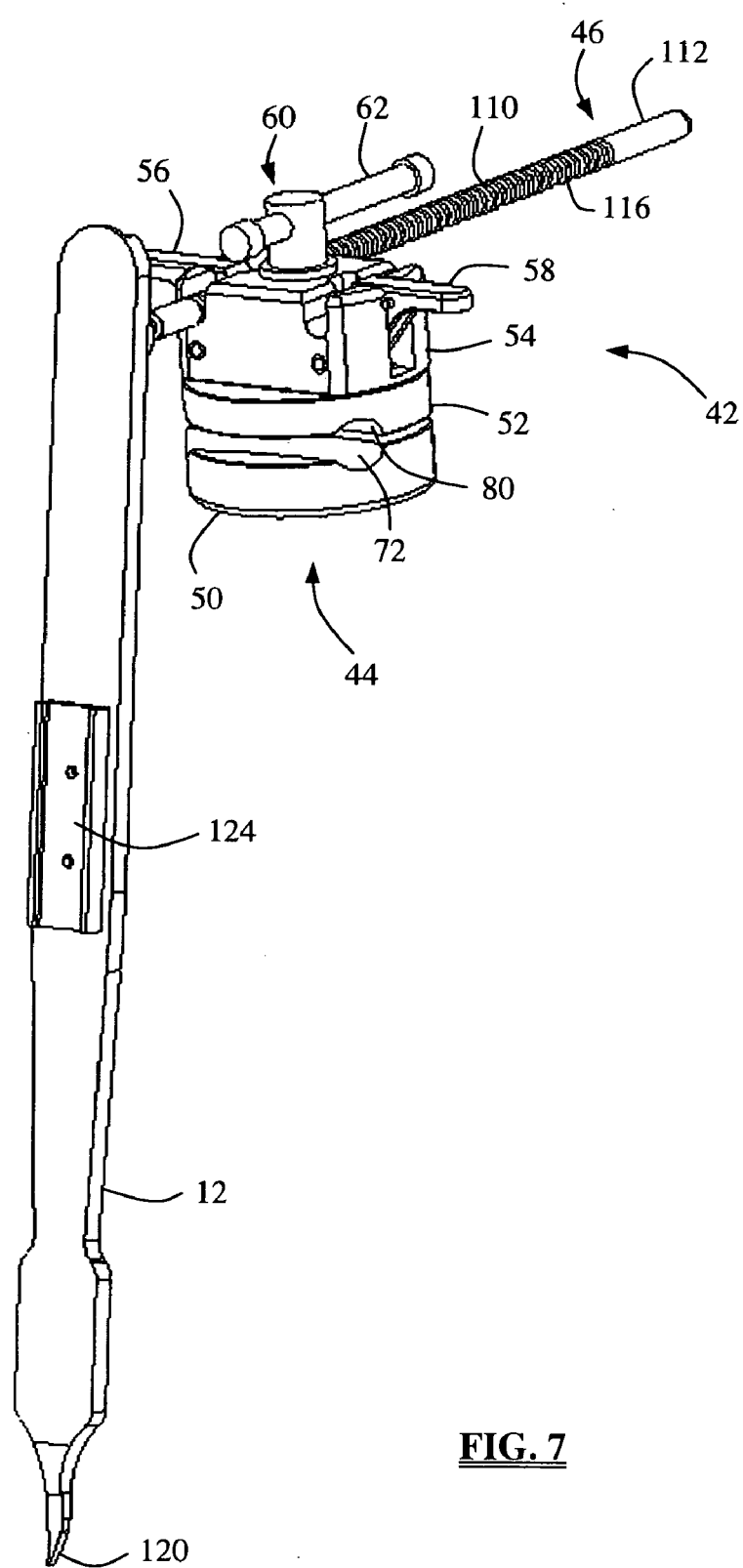
Figure 8:
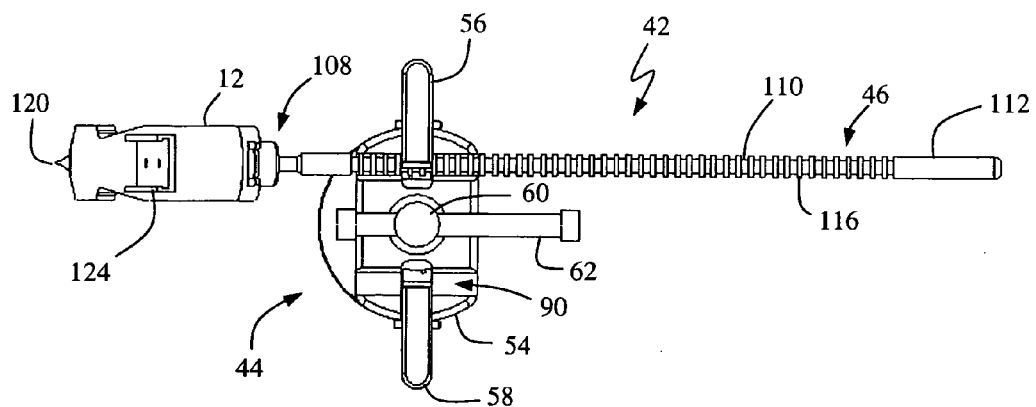
Figure 11:
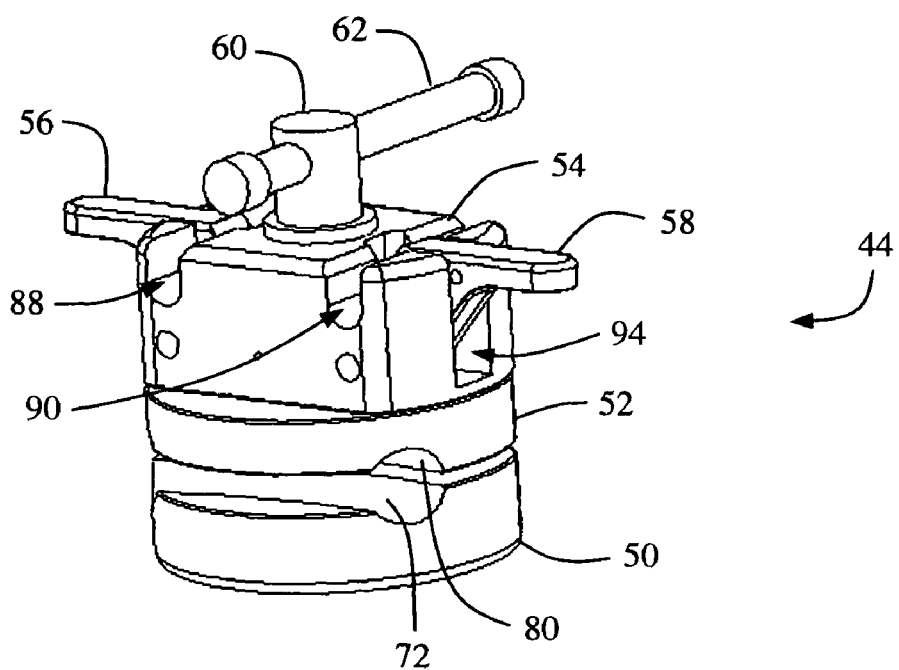
FIG. 11 is a perspective view of a base member of a retractor blade holder assembly of the present invention, with the retractor blade and blade extender removed.
Figure 12:
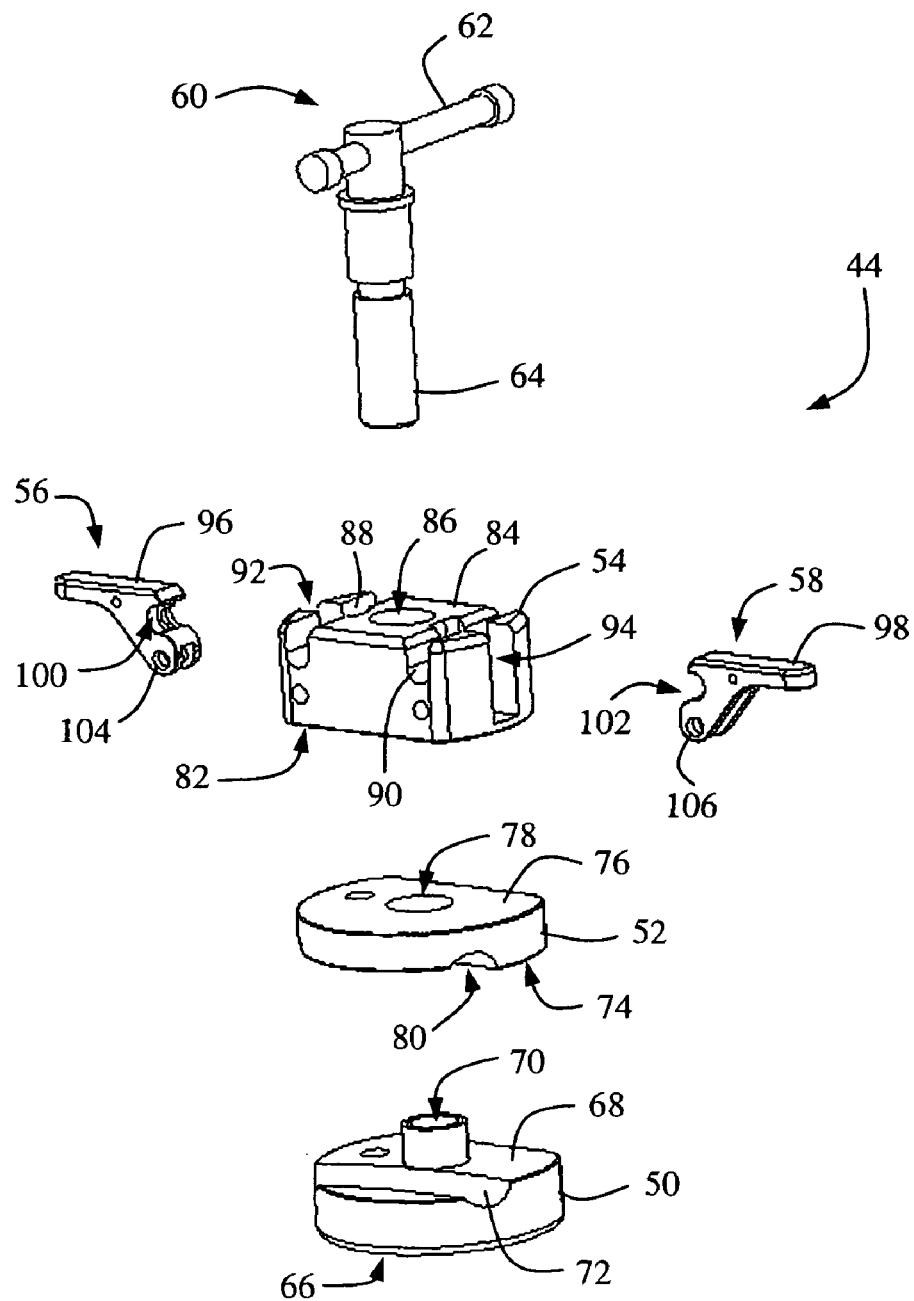
FIG. 12 is an exploded perspective view of the base member of FIG. 11.

FIGS. 6-8 illustrate in detail the construction of each blade holder assembly 42 and blade 12 according to a preferred embodiment of the present invention. Blade holder assembly 42 is dimensioned to slideably engage arm extension 40, and includes a base member 44 and a blade extender 46. Referring to FIGS. 11-12, base member 44 includes a first portion 50, a second portion 52, a third portion 54, pair of clips 56, 58, and a pin member 60. The first portion 50 may be any geometric shape, including by way of example only generally circular, semi-circular, or generally oval. The first portion 50 includes a first generally planar surface 66, a second generally planar surface 68, art aperture 70, and a semi-cylindrical cutout region 72. Aperture 66 extends through the width of the first portion 50 and is dimensioned to receive shaft 64 of pin 60. Semi-cylindrical cutout region 72 is dimensioned to interact with one of arm extensions 40, 41. The second portion 52 may be any geometric shape including by way of example only generally circular, semi-circular, or generally oval, and should have the same general shape as first portion 50. Second portion 52 includes a first generally planar surface 74, a second generally planar surface 76, an aperture 78, and a semi-cylindrical cutout region 80. Aperture 78 extends through the width of the second portion 52, is contiguous with aperture 70, and is dimensioned to receive shaft 64 of pin 60. Semi-cylindrical cutout region 80 is dimensioned to interact with one of arm extensions 40, 41.

The third portion 54 includes a first generally planar surface 82, a second surface 84, a central aperture 86 a pair of first cutout regions 88, 90, and a pair of second cutout regions 92, 94. The third portion 54 may be any geometric shape desired, including by way of example only generally circular, semi-circular, generally oval, generally rectangular, or any combination thereof. Central aperture 86 is generally circular in shape, is contiguous with aperture 78, and is dimensioned to receive shaft 64 of pin 60. The first pair of cutout regions 88, 90 are located generally on second surface 84, are generally semi-cylindrical in shape, and are dimensioned to interact with the elongated blade extenders 46. The second pair of cutout regions 92, 94 are generally rectangular in shape, extend substantially the width of third portion 54, and are dimensioned to receive one of clips 56, 58. The second pair of cutout regions 92, 94 are positioned generally perpendicularly to first pair of cutout regions 88, 90, such that cutout region 92 bisects cutout region 88, and cutout region 94 bisects cutout region 90.

The clips 56, 58 may be any shape necessary to removably secure blade extenders 46 to the base member 42, and are dimensioned to interact with cutout regions 92, 94, respectively. Clips 56, 58 include a generally planar surface 96, 98, a semi-cylindrical surface 100, 102, and an aperture 104, 106, respectively. The semi-cylindrical surface 100, 102 is dimensioned to interact with the elongated blade extenders 46, such that the elongated blade extenders 46 are prevented from migrating in a medial or lateral direction. Apertures 104, 106 are dimensioned such that they enable clips 56, 58 to be secured to the third portion 54. The pin 60 includes an elongated handle portion 62 and a generally cylindrical shaft 64. The generally cylindrical shaft 64 is dimensioned to interact with apertures 70, 78, 86 and traverse the combined widths of the first, second, and third portions 50, 52, 54, respectively. Pin 60 functions to secure the first, second, and third portions 50, 52, 54 to each other, and also to secure blade assembly 42 to one of arm extensions 40, 41.

Referring again to FIGS. 6-8, blade extender 46 includes a medial portion 108, a central elongated shaft 110, and a lateral portion 112. Medial portion 108 is dimensioned to interact with elongated slot 126 of retractor blade 12. The medial portion 108 also includes a pivot 114, which may include any mechanism that allows for changes in the angle defined by the elongated blade extender 46 and the retractor blade 12. By way of example only, the pivot 114 may comprise a ball-and-socket mechanism. The elongated shaft 110 is dimensioned to interact with the semi-cylindrical surfaces 88, 90 of the third portion 54, and semi-cylindrical surfaces 100, 102 of the clips 56, 58. Elongated shaft 110 may include ridges 116 to increase friction to serve as an anti-migration enhancing feature.

Figure 9:
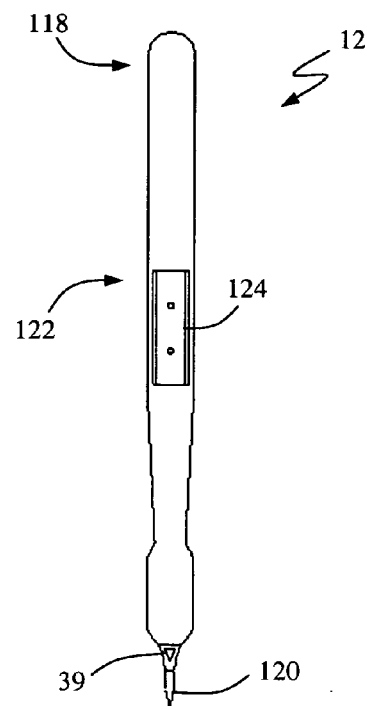
FIGS. 9-10 are front and rear views of a retractor blade according to one embodiment of the present invention.
Figure 10:
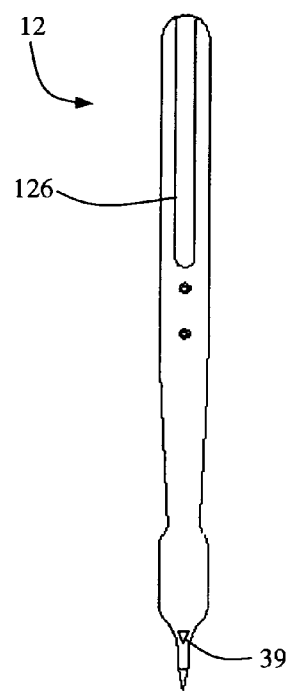

FIGS. 9-10 illustrate in detail each retractor blade 12 according to a preferred embodiment of the present invention. Retractor blade 12 includes a proximal end 118, and distal tip 120, and an elongated portion 122 therebetween. Proximal end 118 includes an elongated slot 126 dimensioned to slideably engage the medial portion 108 of the elongated blade extender 46. The elongated portion 122 may include a utility clip 124, which may optionally interact with a light source (not shown) or other mechanism to aid in the procedure. Distal tip 120 may be generally pointed in nature to enable the distal tip 120 to penetrate a vertebral body in order to secure the retractor blades to the bone. Optionally, the retractor blades 12 may be constructed of suitable material and configuration such that light may be transmitted generally distally through the walls of the retractor blades 12 light to shine light at or near the surgical target site. This may be performed by providing the retractor blades 12 having light-transmission characteristics (such as with clear polycarbonate construction) and transmitting the light almost entirely within the walls of the retractor blades 12 (such as by frosting or otherwise rendering opaque portions of the exterior and/or interior) until it exits a portion along the interior (or medially-facing) surface of the retractor blade to shine at or near the surgical target site. The exit portion may be optimally configured such that the light is directed towards the approximate center of the surgical target site and may be provided along the entire inner periphery of the retractor blade 12 or one or more portions therealong.

In use, a surgeon may initiate the ALIF procedure by surgical techniques generally known and commonly used in the art. This common procedure includes establishing a small operative corridor by making an incision, clearing the relevant anatomy, and reaching the vertebral body. At this point, a plurality of retractor blades may be inserted such that the distal portions 120 penetrate the targeted vertebral body or bodies in a desired location. Once the retractor blades 12 are inserted in the proper locations, a handle assembly 20 of the present invention may be provided in a "closed" position (preferably rigidly coupled in a fixed relation to the operative site, such as through the use of an articulating arm mounted to the operating table). Before coupling the retractor blades 12 to the handle assembly 20, the blade assemblies 42 should be positioned in the desired locations along arm extensions 40, 41. When the blade assemblies 42 are properly positioned and secured by tightening pin 60, the handle assembly 20 may be mated to the retractor blades 12 by inserting medial portions 108 of blade extenders 46 into elongated slots 126. Once the handle assembly 20 and the retractor blades 12 are sufficiently mated, the operative corridor 15 may be opened by manipulating the handle extenders 31, 33 to cause the arms 26, 28 to move away from one another. By extension, the plurality of retractor blades 12 also move away from one another, thus expanding the operative corridor 15.

The present invention involves accessing a surgical target site in a fashion less invasive than traditional "open" surgeries. In addition to the features set forth above, the tissue retraction assembly 10 of the present invention may be equipped with one or more electrodes for use in detecting the existence of (and optionally the distance and/or direction to) neural structures associated with the surgical target site or accessing the surgical target site. For example, any or all of the retractor blades 12 may be provided with one or more electrodes 39 (preferably at their distal regions) as shown in FIGS. 9-10. These electrodes are preferably provided for use with a nerve surveillance system such as, by way of example, the type shown and described in the following commonly assigned and co-pending applications: PCT App. Ser. No. PCT/US02/22247, entitled "System and Methods for Determining Nerve Proximity, Direction, and Pathology During Surgery," filed on Jul. 11, 2002; PCT App. Ser. No. PCT/US02/30617, entitled "System and Methods for Performing Surgical Procedures and Assessments," filed on Sep. 25, 2002; PCT App. Ser. No. PCT/US02/35047, entitled "System and Methods for Performing Percutaneous Pedicle Integrity Assessments," filed on Oct. 30, 2002; and PCT App. Ser. No. PCT/US03/02056, entitled "System and Methods for Determining Nerve Direction to a Surgical Instrument," filed Jan. 15, 2003 (collectively "Neurovision PCT Applications"), the entire contents of which are incorporated by reference into the present application as if expressly disclosed herein. Generally speaking, this nerve surveillance system is capable of detecting the existence of (and optionally the distance and/or direction to) neural structures during the distraction and retraction of tissue by detecting the presence of nerves by applying a stimulation signal to such instruments and monitoring the evoked EMG signals from the myotomes associated with the nerves being passed or approached by the retraction system of the present invention. In so doing, the system as a whole (including the surgical access system of the present invention) may be used to form an operative corridor through (or near) any of a variety of tissues having such neural structures, particularly those which, if contacted or impinged, may otherwise result in neural impairment for the patient. In this fashion, the access system of the present invention may be used to traverse tissue that would ordinarily be deemed unsafe or undesirable, thereby broadening the number of manners in which a given surgical target site may be accessed.

The surgical access system of the present invention can be used in any of a wide variety of surgical or medical applications, above and beyond the spinal applications discussed herein. Such spinal applications may include any procedure wherein instruments, devices, implants and/or compounds are to be introduced into or adjacent the surgical target site, including but not limited to discectomy, fusion (including PLIF, ALIF, TLIF and any fusion effectuated via a lateral or far-lateral approach and involving, by way of example, the introduction of bone products (such as allograft or autograft) and/or devices having ceramic, metal and/or plastic construction (such as mesh) and/or compounds such as bone morphogenic protein), total disc replacement, etc. . . . ).

What is claimed is:

1. A system for accessing a surgical target site, comprising:
   a handle assembly including a first arm member hingedly coupled to a second arm member, said first arm member having a first recess formed within a distal end thereof, said second arm member having a second recess formed within a distal end thereof;
   a first elongated extension member removably coupled to said first arm member, said first elongated extension member having a post extending from a proximal end of said first elongated extension member, said post being received within said first recess to removably couple said first elongated extension member and said first arm member;
   a second elongated extension member removably coupled to said second arm member, said second elongated extension member having a post extending from a proximal end of said second elongated extension member, said post being received within said second recess to removably couple said second elongated extension member and said second arm member;
   a plurality of blade holder assemblies slideably and rotatably coupled to said first and second elongated extension members, said first and second elongated extension members having a generally circular cross-section to enable the rotation of said blade holder assemblies; and
   a plurality of blades, each of said blades configured to be coupled to one of said blade holder assemblies while in a closed position and thereafter selectively opened to create a customized operative corridor to said surgical target site.

2. The system of claim 1, wherein at least one of said first and second elongated extension members has a generally arcuate shape.

3. The system of claim 1, wherein each of said plurality of blade holder assemblies comprises:
   a base member configured to slideably receive a portion of one of said first and second elongated extension members; and
   an elongated member adjustably coupled to said base member and having an end portion dimensioned to engage at least one of said plurality of blades.

4. The system of claim 3, wherein said elongated member further includes at least one anti-migration feature.

5. The system of claim 4, wherein said anti-migration feature comprises a plurality of ridges.

6. The system of claim 1, wherein each of said plurality of blades includes a shaped distal end.

7. The system of claim 6, wherein said shaped distal end is generally pointed.

8. The system of claim 1, wherein at least one of said plurality of blades is adapted for providing light near said surgical target site.

9. The system of claim 8, wherein said at least one of said plurality of blades is coupled to at least one light source.

10. The system of claim 8, wherein said at least one of said plurality of blades is constructed from clear polycarbonate.

11. The system of claim 1, wherein at least one of said plurality of blades includes at least one stimulation electrode.

12. The system of claim 1, wherein said surgical target site comprises a spinal target site.

13. The system of claim 1, further comprising a first and second locking elements configured to lock said first and second elongated extension members to said first and second arm members.

14. The system of claim 13, wherein said first and second locking elements comprise first and second set screws, respectively.

15. The system of claim 14, wherein:
said first set screw is received within a first aperture formed near said distal end of said first arm member, said first aperture in communication with said first recess; and
said second set screw is received within a second aperture formed near said distal end of said second arm member, said second aperture in communication with said second recess.

16. A method of accessing a surgical target site, comprising the steps of:
(a) introducing a plurality of retractor blades into a surgical target site while in a closed position;
(b) coupling said plurality of retractor blades to a plurality of blade holder assemblies;
(c) attaching said blade holder assemblies to a handle assembly including a first arm member hingedly coupled to a second arm member, said first arm member having a first recess formed within a distal end thereof, said second arm member having a second recess formed within a distal end thereof, said handle assembly further including first and second shaped extension members removably coupled to said first and second arm members, said first and second shaped extension members each having a post extending from a proximal end thereof, said post of said first shaped extension member being received within said first recess to couple said first shaped extension member and said first arm member, said post of said second shaped extension member being received within said second recess to couple said second shaped extension member and said second arm member, each of said first and second elongated extension members having a generally circular cross-section to enable the rotation of said blade holder assemblies; and
(d) selectively opening said plurality of retractor blades to create a customized operative corridor to said surgical target site.

17. The method of claim 16, wherein each of said retractor blades comprises a pointed end.

18. The method of claim 17, wherein introducing a plurality of retractor blades into a surgical target site comprises penetrating at least one targeted vertebral body with said pointed ends of said plurality of retractor blades.

19. The method of claim 16, wherein at least one of said first and second shaped extension members has a generally arcuate shape.

20. The method of claim 16, wherein each of said plurality of blade holder assemblies comprises:

a base portion configured to slideably receive a portion of one of said first and second shaped extension members; and
an elongated member adjustably coupled to said base portion and having an end portion dimensioned to engage at least one of said plurality of blades.

21. A method of accessing a spinal target site, comprising the steps of:
providing a tissue retraction assembly in a closed position, said tissue retraction assembly having a handle assembly and a plurality of blade holder assemblies, said handle assembly including a first arm member hingedly coupled to a second arm member, each of said first and second arm members having a recess formed within a distal end thereof, said first arm member further including a first shaped extension member coupled thereto, the first shaped extension member including a first post extending from a proximal end thereof, said first post being received within said first recess to couple said first shaped extension member and said first arm member, said second arm member further including a second shaped extension member coupled thereto, the second shaped extension member including a second post extending from a proximal end thereof, said second post being received within said second recess to couple said second shaped extension member and said second arm member, said blade holder assemblies each comprising a base portion and an elongated member, wherein said base portion is slideably attached to one of said first and second extension members, said first and second extension members each having a generally circular cross-section to enable the rotation of said blade holder assemblies;
introducing a plurality of retractor blades into said spinal target site while in a closed position;
coupling each of said plurality of retractor blades to an end portion of at least one elongated member; and
selectively opening said plurality of retractor blades to create a customized operative corridor to said spinal target site.

22. The method of claim 21, further comprising:
coupling said elongated member to said base portion.

23. The method of claim 21, wherein each of said plurality of retractor blades includes a pointed end.

24. The method of claim 23, wherein introducing a plurality of retractor blades into said spinal target site comprises penetrating at least one vertebral body with said pointed end of at least one retractor blade.

* * * * *